United States Patent [19]

Carson

[11] 4,414,962
[45] Nov. 15, 1983

[54] OPERATING ARTHROSCOPE

[76] Inventor: Robert W. Carson, 1419 Circle Way, Salt Lake City, Utah 84103

[21] Appl. No.: 109,150

[22] Filed: Jan. 2, 1980

Related U.S. Application Data

[63] Continuation-in-part of Ser. No. 806,833, Jun. 15, 1977, and Ser. No. 861,632, Dec. 19, 1977.

[51] Int. Cl.³ .............................................. A61B 1/06
[52] U.S. Cl. ..................................................... 128/6
[58] Field of Search ........................................ 128/4-9, 128/303.15, 326; 350/96.26; 356/241

[56] References Cited

U.S. PATENT DOCUMENTS

| | | | |
|---|---|---|---|
| 1,150,214 | 8/1915 | London | 128/7 |
| 2,120,996 | 6/1938 | Wappler | 128/7 |
| 2,129,391 | 9/1938 | Wappler | 128/6 |
| 2,487,498 | 11/1949 | Wallace | 128/7 |
| 2,932,294 | 4/1960 | Fourestier et al. | 128/6 |
| 3,261,351 | 7/1966 | Wallace | 350/96.26 |
| 3,703,169 | 11/1972 | Ouchi | 128/6 |
| 3,830,225 | 8/1974 | Shinnick | 128/6 |
| 3,945,375 | 3/1976 | Banko | 128/6 |
| 3,994,557 | 11/1976 | Hopkins | 128/4 |
| 4,024,858 | 5/1977 | Chikama | 128/4 |
| 4,103,680 | 8/1978 | Yoon | 128/326 |
| 4,203,444 | 5/1980 | Bonnell et al. | 128/305 |
| 4,217,891 | 8/1980 | Carson | 128/6 |
| 4,261,346 | 4/1981 | Wetterman | 128/6 |
| 4,267,828 | 5/1981 | Matsuo | 128/6 |

FOREIGN PATENT DOCUMENTS

| | | | |
|---|---|---|---|
| 1900017 | 8/1970 | Fed. Rep. of Germany | 128/6 |
| 2545761 | 4/1977 | Fed. Rep. of Germany | 128/303.15 |

OTHER PUBLICATIONS

"Sterilization", Medical World News, Sep. 21, 1973, pp. 40-50.

Primary Examiner—Kyle L. Howell
Assistant Examiner—Max F. Hindenburg
Attorney, Agent, or Firm—Trask & Britt

[57] ABSTRACT

An arthroscope is constructed with a flattened thin cross-section as viewed from its distal end. The sheath of the arthroscope as viewed normal a plane intersecting the occular lens and the instrument channel is offset at a central housing which contains the entry to the instrument channel. The occular lens is vertically remote from the entry to the instrument channel.

16 Claims, 11 Drawing Figures

OPERATING ARTHROSCOPE

RELATED PATENT APPLICATIONS

This application is a continuation-in-part of Ser. Nos. 806,833, filed June 15, 1977, entitled "Arthroscopic Surgical Apparatus and Method", and 861,632, filed Dec. 19, 1977, entitled "Novel Arthroscope."

The parent applications disclose apparatus and methods useful for arthroscopic examinations and surgical procedures. The apparatus described and claimed in Ser. No. 861,632 finds use in conjuction with the apparatus and methods of Ser. No. 806,833. The feature of principal importance to the operation of Ser. No. 861,632 is the distal end configuration of the sheath. The present disclosure is principally concerned with the configuration of the sheath as viewed from the side. It is also concerned with arrangement of occular and other components to provide for increased efficiency in use. The disclosures of both parent applications are incorporated by reference.

BACKGROUND OF THE INVENTION

1. Field

This invention pertains to endoscopes in general and to arthroscopes in particular. Specifically, it provides such an instrument in a configuration which avoids the discomfort, fatigue and confusion involved with the use of conventional endoscopes, such as operating arthroscopes.

2. State of the Art

Endoscopy is the art of examining the interior of a body cavity or hollow organ by the use of a slender tubular telescopic instrument called an "endoscope." Endoscopes have been in common use since the early twentieth century. These instruments include a lens system, which may be conventional glass lenses within a rigid tube, air spaces between glass rods shaped to configurate the entrapped air pockets as lenses, optical glass fibers combined with conventional lenses, or other means; and a lighting system, which may be a direct illumination system (e.g., a tungsten light bulb) but is more often fiber light (light transferred from an external source through optical glass fibers). Endoscopes also commonly contain an irrigation system for introducing fluids, typically normal saline solution, to the region being examined. These systems are all contained within a cylindrical tubular housing, usually called a "sheath", which may be flexible, but is more often rigid. The cross-sectional configuration of the sheath normal its longitudinal axis (that is, as viewed from the distal end of the endoscope) is traditionally circular.

Examples of modern endoscopes are disclosed by United Kingdom Pat. No. 719,538 and by U.S. Pat. Nos. 3,525,332; 3,599,630; 3,608,547; 3,730,632; 3,744,906; 3,799,150; 3,818,902; 3,819,267; 3,889,662; and 4,024,858. Other U.S. patents of interest include U.S. Pat. Nos. 1,703,216; 1,747,407 and 2,120,996.

Endoscopes have been used for arthroscopic examinations for several decades. The development of arthroscopy and instruments adapted for arthroscopic examinations (arthroscopes) is described in the monograph "Arthroscopy of the Knee", Robert W. Jackson and David J. Dandy, Modern Orthopedic Monographs, 1976 Grune & Stratton, Inc., New York. From the monograph, it is apparent that the principal objective sought in developing arthroscopes has been to reduce their diameter compared to earlier endoscopes. All of the components conventional to an endoscope, namely an optical system, a lighting system, an irrigation system, and often an instrument channel, are contained within a usually rigid cylindrical sheath of approximately circular cross-section. The Watanabe 22 shown in FIG. 2–5 of the monograph utilizes a sheath slightly oval in cross-section to accommodate two crescentic bundles of light fibers for illumination. The grouping of the light fibers in this fashion is to avoid the penumbra typically present in the center of the visual field.

Examination of the knee joint, or other joints, imposes certain restrictions on procedures not normally encountered with other endoscopic examinations. For example, a persistent problem is arthroscopy has been maintaining adequate sterility. A circular cross-section is appropriate for introduction into the orifices of the genitourinary and gastrointestinal tracts or for puncturing the abdominal wall, but the introduction of conventional round arthroscopes to the knee joint tends to be traumatic because of the limited spacing between bones. Conventional arthroscopes of small cross-section are susceptible of breakage if the knee is flexed or if too much force is applied in efforts to distract the joint using the arthroscope as a lever or fulcrum. In the past, less delicate arthroscopes have necessarily been constructed within sheaths of greater diameter.

Characteristically, the use of conventional operating arthroscopes, as well as other endoscopes, requires the manipulation of instruments from the vicinity of the surgeon's ear. This practice is both awkward and fatiguing, but it is imposed by the customary location of the entry to the instrument channel at approximately the same level as the occular lens. It has long been recognized that there exists an optimum visual area for cognitive efforts and work. For example, C. T. Morgan has dilineated boundaries for the normal line of sight in the publication *The Human Engineering Guide to Equipment Design. The Human Body in Equipment Design,* McCormick, McGraw Hill (1976) recognizes that blind positioning movements in different directions from the body are made most accurately when they are to be straight ahead and are to be made below shoulder level. Nevertheless, currently available operating arthroscopes are structurally arranged in a fashion which forces the surgeon to maneuver instruments outside the norms established as optimum by such studies. The problems of discomfort, inefficiency, fatigue, and decreased accuracy inherent in conventional endoscopes, are compounded by the use of surgical instruments a foot or more in length. Instruments of such length are required because of the long instrument channels of conventional endoscopes.

Even those endoscopes (such as the O'Conner operating arthroscope marketed by Richard Wolf Medical Instruments Corp. of Rosemont, Ill.) with offset viewing lenses retain the disadvantages referred to herein. The instrument channels of such scopes are arranged for entry at a horizontal plane close to that of the surgeon's eye. Moreover, considerable leverage is provided by a lateral extension of the barrel which carries the lens system. This leverage tends to multiply forces applied to the viewing end of the arthroscope as those forces are translated to movement of the distal end of the scope itself or surgical apparatus associated with the scope. Unless precautions are both observed and effective, such high-force motion can be injurious to the patient, the surgical apparatus, or both.

SUMMARY OF THE INVENTION

The arthroscope of this invention departs substantially from the structural concepts traditional to endoscopes. The instrument provides the necessary components for operating (lens system, light system, instrument channel and usually an irrigation system) within a sheath housing having a cross-sectional configuration (taken normal the major axis of the arthroscope) which may be circular or oval, but is most preferably "flattened" in cross-section; that is, shaped as either a parallelogram or a modified parallelogram with a pair of approximately parallel longer sides and a pair of shorter sides which may also, but need not be parallel. The aforedescribed cross-sectional configuration is perceived by viewing the arthroscope from its distal end. Of substantial importance in the preferred embodiments is that the spacing between the longer sides (referred to as the "thickness" of the instrument) be as small as possible, having due regard to the space requirements of the components within the sheath. In an operating arthroscpe, the component of largest minimum acceptable size is usually the instrument channel. The cross-sectional spacing between the longest sides of the sheath need then be just sufficient to accommodate this component. Operating arthroscopes constructed in accordance with this invention will typically be less than about 5 millimeters thick, and preferably less than about 4 millimeters thick.

Although the instruments of this invention are purposely constructed as thin as possible, the spacing between the short sides of the cross-section, (referred to as the "width" of the instrument) may be relatively large. That is, considerable freedom of width is permissible to accommodate a number of structural features not available with conventional arthroscopes. By way of illustration, the width of the instrument may be enlarged to accommodate additional optic fibers, if greater brilliance at the operational site is desired. This feature has application in instruments adapted for photography or to incorporate teaching attachments, for example. For most applications, adequate lighting is provided when the cross-sectional area of the optic fibers in the sheath approximately equals the cross-sectional area of the objective lens. Freedom of width also permits adaption of the distal end of the arthroscope as a retractor to move the synovium or the fat pad aside. Moreover, the instrument channel may be shaped to pass relatively wide instruments, thereby obviating one of the limitations heretofore imposed on the design of surgical instruments used with arthroscopes.

One of the inherent difficulties of mastering arthroscopic techniques has been the lack of depth perception provided by conventional arthroscopes. The increased width permitted by the present invention offers two means for improving on this situation. First, depth perception and perspective at the operative site is enhanced by increasing the lateral spacing of the objective lens from the distal termination of the instrument channel. Ideally, the optics will be spaced as far as possible from the instrument channel; that is, at the extreme ends of the major axis (allowing for only a few optic fibers between the lens and the sheath). The surgeon thus observes the instrument approaching the operative site at an angle rather than directly in his line of sight. Moreover, it is highly preferred that the line of sight of the optic system be angled about 15 to about 30 degrees toward the instrument channel to further improve perspective. It is also within contemplation to mount a second lens system within the sheath, spaced from the first lens system, thereby providing true binocular vision. Any of these expedients will enable many more surgeons to become skillful at arthroscopic surgery, and should also permit the development of more intricate diagnostic and surgical procedures.

Of paramount importance, the "thinness" of the arthroscopes of this invention permits more thorough examination of joints with greater accuracy. The potential for false negative readings is greatly reduced. (A "negative" reading means that nothing wrong is observed.) The claimed arthroscopes often can probe to the interior of a joint without mechanically distracting the joint as in current practice.

The aforedescribed advantages are achieved with an attendant reduction of trauma to the patient. First, the soft tissues which must be penetrated to gain access to the joint space suffer markedly reduced trauma through use of this invention. Of even greater significance, from the standpoint of present experience in the art, the present invention causes less trauma to the cartilage surface of the joint. In those instances when the tip of the arthroscope is used as a fulcrum, e.g., to pry open the back of a knee joint, the forces are spread over a larger surface area, thereby avoiding damage both to the cartilage and the instrument. The sheath of the claimed arthroscopes may be thicker than is now conventional. Moreover, it is practical to contour and polish the sheath exterior to avoid laceration of the cartilage surfaces.

A further modification offered by this invention to conventional design resides in the configuration of the scope as viewed normal its vertical axis. According to this invention a segment, including the viewing end, of the scope is offset slightly (usually about 2 to about 5 centimeters) from the remainder of the barrel of the scope, including the instrument channel. The offset segment is sufficiently long that the occular lens, and thus the surgeon's eye, is held well above the entry to the instrument channel. This arrangement permits the use of much shorter instruments; and even more importantly, permits the manipulation of the instruments with the surgeon's hands located within a comfortable and natural working zone. This zone is generally below eye level and forward of the surgeon's torso. With reference to a plane perpendicular to the vertical plane through the surgeon's shoulders, the present construction permits the surgeon's hands to remain well within the 45 degree angle generally regarded as the normal work angle. Most manipulations may be accomplished in the ideal zone for blind manipulations; that is, straight ahead (in front of the torso) and below shoulder level. The lateral offset is just sufficient to permit passage of instruments without contamination by the surgeon's head.

BRIEF DESCRIPTION OF THE DRAWINGS

In the drawings, which illustrate what is presently regarded as the best mode for carrying out the invention.

DESCRIPTION OF THE ILLUSTRATED EMBODIMENTS

Figure 1:
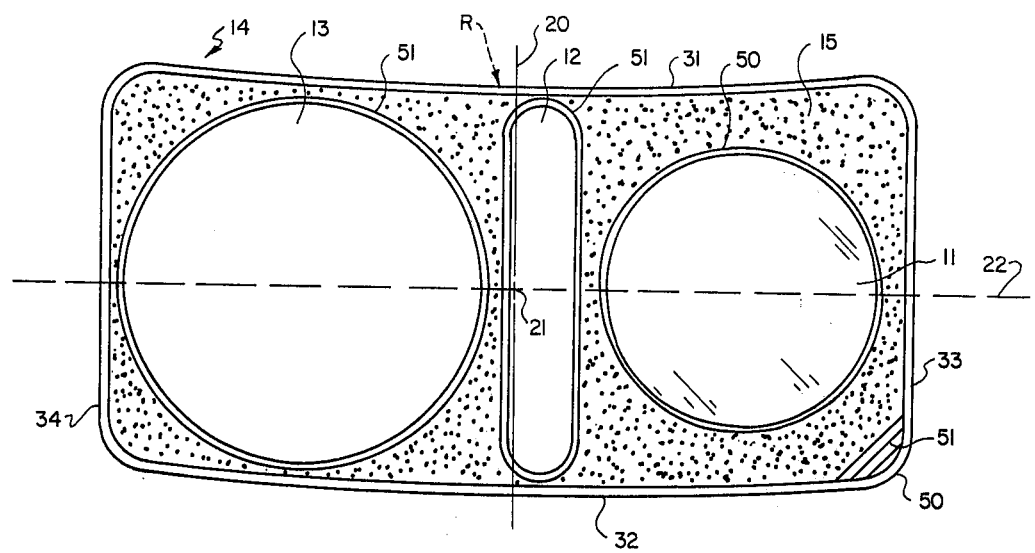
FIG. 1 is a typical operating arthroscope of this invention viewed from its distal end and showing the arrangement of its components.

The operating arthroscope illustrated by FIG. 1 comprises a lens system, the objective lens 11 of which is visible from the distal end of the instrument; an irrigation system, including the conduit 12; and an instrument channel 13; arranged within a rigid sheath 14. The interstitial spaces between the components 11, 12 and 13 and within the sheath 14 are packed with light-transmitting optic fibers 15.

The arthroscope of FIG. 1 is constructed in generally conventional fashion except for the cross-sectional shape of the sheath 14 and the arrangement of the components 11, 12, 13 and 15 housed within the sheath 14. As viewed from its distal end, the cross-section of the arthroscope may be considered as having a minor axis, represented by line 20, which intersects its geometric center 21; and a major axis, represented by the line 22, normal the minor axis 21 at the center 21. The distal ends of instruments with regular cross-sections will be bisected into two congruent parts by the minor axis 20 as shown.

The sheath 14 is of rigid, e.g., stainless steel, construction, and includes two relatively long side walls 31, 32 and two relatively short side walls 33, 34. The side walls 31, 32 which intersect the minor axis 20 are approximately parallel. According to certain embodiments, these side walls 31, 32 are arcuate, as shown, to approximately match the surface contours of the bones in a joint. In the illustrated instance, the radius of curvature R is approximately 2.5 centimeters, side wall 31 is concave and side wall 32 is convex. The short side walls 33, 34 may also be approximately parallel, as shown, and are ideally as short as possible; usually just long enough to provide the minimum spacing required between the side walls 31 and 32 to contain the largest system housed in the sheath 14 (the instrument channel 13, FIG. 1; or the lens system 41, FIG. 2).

The width (that is, the spacing of the side walls 33 and 34), of the instrument is selected to provide adequate cross-sectional area for the irrigation system (water channels 1, FIG. 1 and 42, FIG. 2) desired; the lighting system (optical fibers 15, FIG. 1 and 45, FIG. 2); and any other systems which may be included within the sheath. Typical operating arthroscopes of this invention are between about 3 to about 5 millimeters thick, desirably less than about 4.5 millimeters thick.

For applications requiring greater strength, the corners 50 connecting side walls, e.g., 32 and 33, may be structurally reinforced, e.g., by thickening the sheath as shown 51. The lenses 11, 41 are shown contained within rigid tubes 50, e.g., of structural plastic or metal. The various channels 12, 13, 42 are typically defined by similar rigid tubes or conduit 51.

EXAMPLE I

The operating arthroscope illustrated by FIG. 1 may be constructed within a sheath 14 measuring about 3½ by about 7 millimeters in cross-section to house a lens system with a 2.4 mm objective lense 11, a 3 mm instrument channel 13, a generous water channel 12, and ample optical fibers 15.

EXAMPLE II

Figure 2:
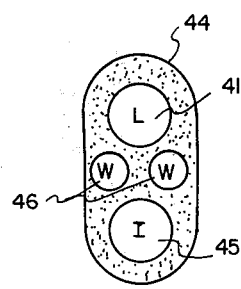
FIG. 2 is a similar view of an alternative sheath configuration.

The operating arthroscope shown by FIG. 2 may be constructed within a sheath 44 measuring approximately 4 by about 7 millimeters. The instrument channel 45 is about 3.5 mm long. The lens system is such an instrument could have an objective lens 41 as large as about 3 mm and irrigation channels 46 of ample size.

EXAMPLE III

Figure 3:
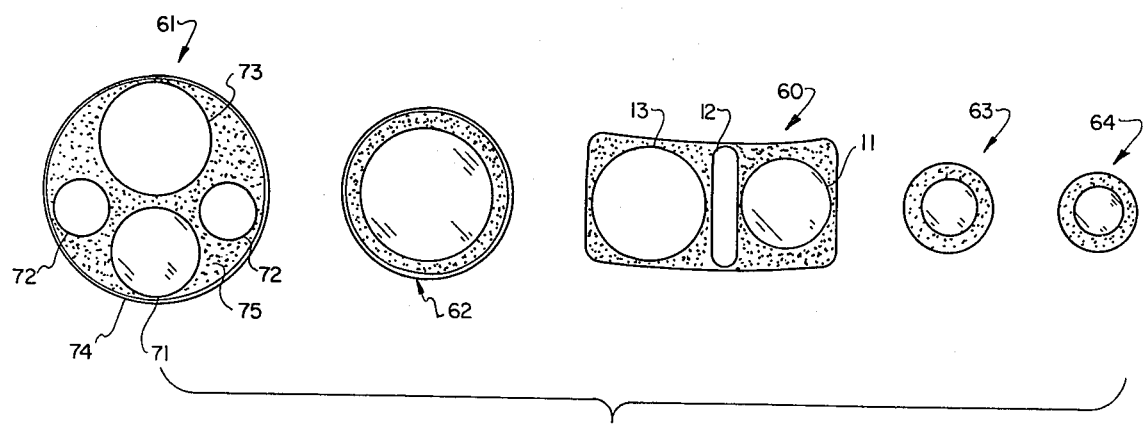
FIG. 3 is a similar view of the arthroscope of FIG. 1 together with a series of prior art instruments drawn to the same scale.

FIG. 3 compares the relative cross-sections of an instrument 60 constructed as shown in FIG. 1 and described in EXAMPLE I with a series 61, 62, 63 and 64 of conventional instruments in current use. By way of comparison, the currently used instrument 61 (a Wolf operating arthroscope) contains a 2.5 mm objective lens 71, a 3 mm instrument channel 72 and a pair of irrigation channels 73 within a circular cylindrical sheath 74 packed with sufficient optic fiber 75 to provide adequate illumination. The sheath 74 is 6.5 mm in diameter. The thickness of the instrument of EXAMPLE I is only slightly over half (about 54%) the diameter of the comparable Wolf instrument, and provides for better irrigation at the operative site. The cross-sectional area of the instrument of EXAMPLE I is also significantly (more than 20%) smaller, thereby requiring a smaller puncture wound for insertion.

The other instruments 62, 63, 64 illustrated by FIG. 3 have diameters of 5, 2.5 and 2.2 millimeters, respectively, but include neither instrument nor irrigation channels. These instruments include only lenses and optical fiber lighting systems, and are useful for diagnostic applications only.

Figure 4:
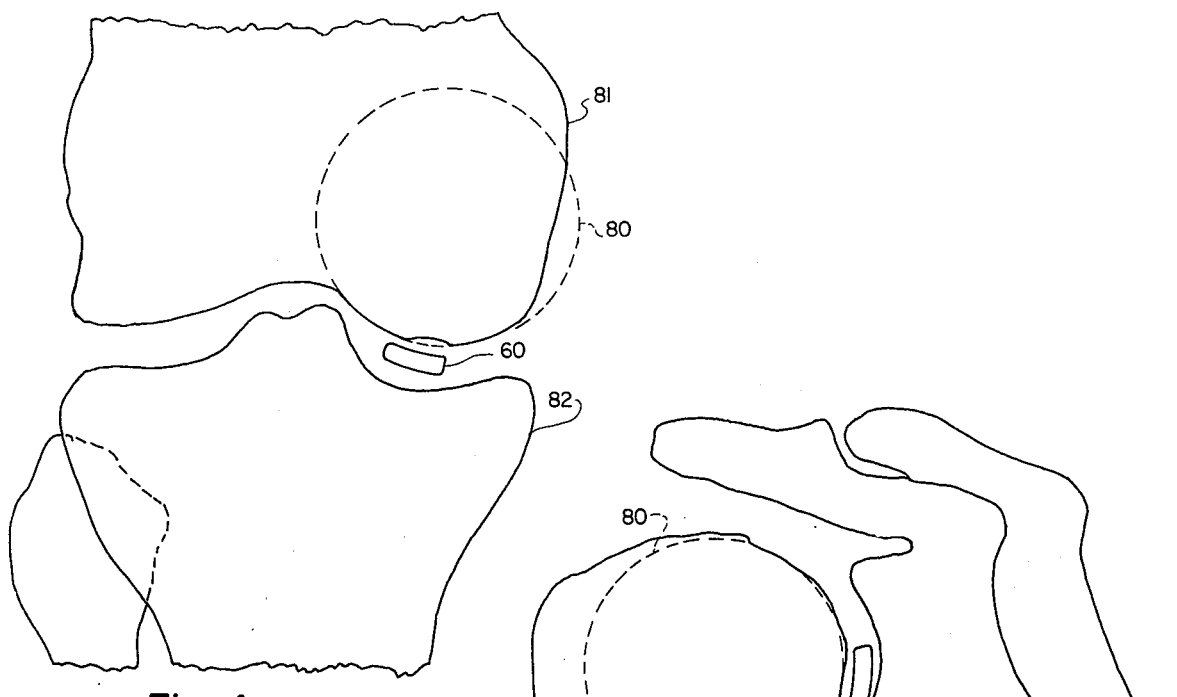
FIGS. 4 through 6 illustrate various joints with an arthroscope of this invention in place.
Figure 5:
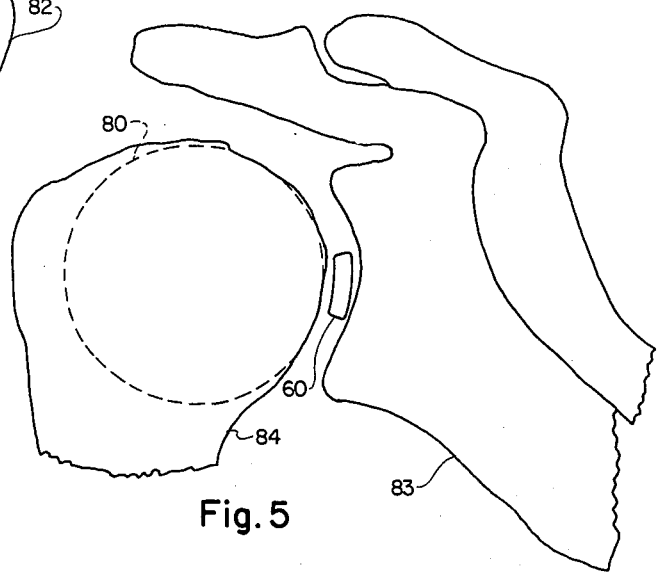
Figure 6:
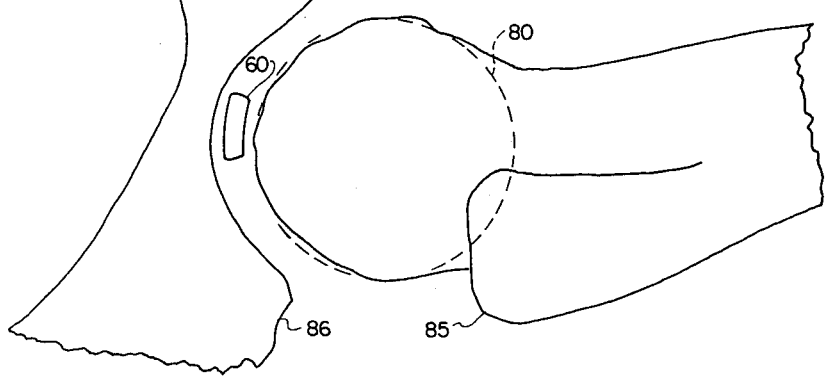

FIGS. 4, 5 and 6 illustrate the placement of an arthroscope 60, constructed as taught by EXAMPLE I, within a knee joint, shoulder joint and hip joint, respectively. The joints are shown in connection with a reference circle 80. Typical mature joints from the same male individual are illustrated compared to a reference circle with a radius of approximately 2½ centimeters. Of course, the joints of various individuals differ somewhat in size and configuration. Nevertheless, as may be seen from the drawings, a single arthroscope of standardized dimension can be used in all of the major joints of the majority of the human population.

Within tolerable limits, the sockets defined by the femur 81 and tibia 82 of the knee; the scapula 83 and humerus 84 of the shoulder; and the femur 85, ilium 86 and pubis 87 of the hip are generally similar in configuration in a given individual. Accordingly, relative few arthroscopic instruments constructed in accordance with this invention are sufficient for a complete diagnostic and treatment service of these joints.

Figure 7:
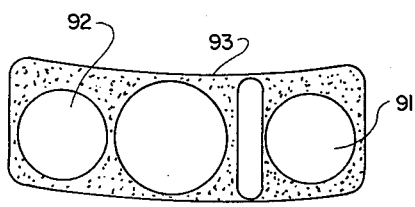
FIG. 7 shows a binocular version of an operating scope of this invention viewed from its distal end.

The binocular version illustrated by FIG. 7 includes a pair 91, 92 of lens systems spaced along the major axis of the cross-section of the barrel 93. Whether a single lens system or a double system is used, perspective is improved by separating the lenses as far as practicable from the instrument channel. Preferably the objective lens is angled toward the instrument channel for a further enhancement of binocular vision. Angles of about 15 to about 30 degrees from a line parallel the vertical axis of the instrument channel are satisfactory for this purpose. Moreover, it has been found that when a lens is angled towards the light it is not necessary to surround the lens with optic fibers to avoid the penumbra effect.

Referring specifically to FIGS. 8 through 11, an operating arthroscope is constructed with a first barrel segment 101 terminating at the bottom of a central housing, designated generally 102; and a second barrel segment 103, extending upward from the central housing 102. As illustrated, the bottom of the arthroscope is oriented to the top of the figures. An instrument channel 104 extends upward from the housing 102 in line with the bottom segment 101. The bottom segment 102 is desirably relatively short; e.g., about 8 to about 10 centimeters so that relatively short instruments can be used. The conventional water valve 105 shown may be replaced with a short watergate arrangement to further decrease the total length of the instrument channel. The length of the top segment 103 should be sufficiently longer than the bottom segment to permit the insertion of instruments through the instrument channel 104 without contacting the surgeon's face in the vicinity of the eye piece 106. The ocular lens should thus be spaced from the entry to the instrument channel by a distance no less than (usually a few centimeters greater than) the distance from the entry to the distal end of the instrument channel.

A connector 107 for a light source extends from the housing 102, as does a valve 108 for an irrigation fluid, such as normal saline.

Figures 8, 9, 10, 11:
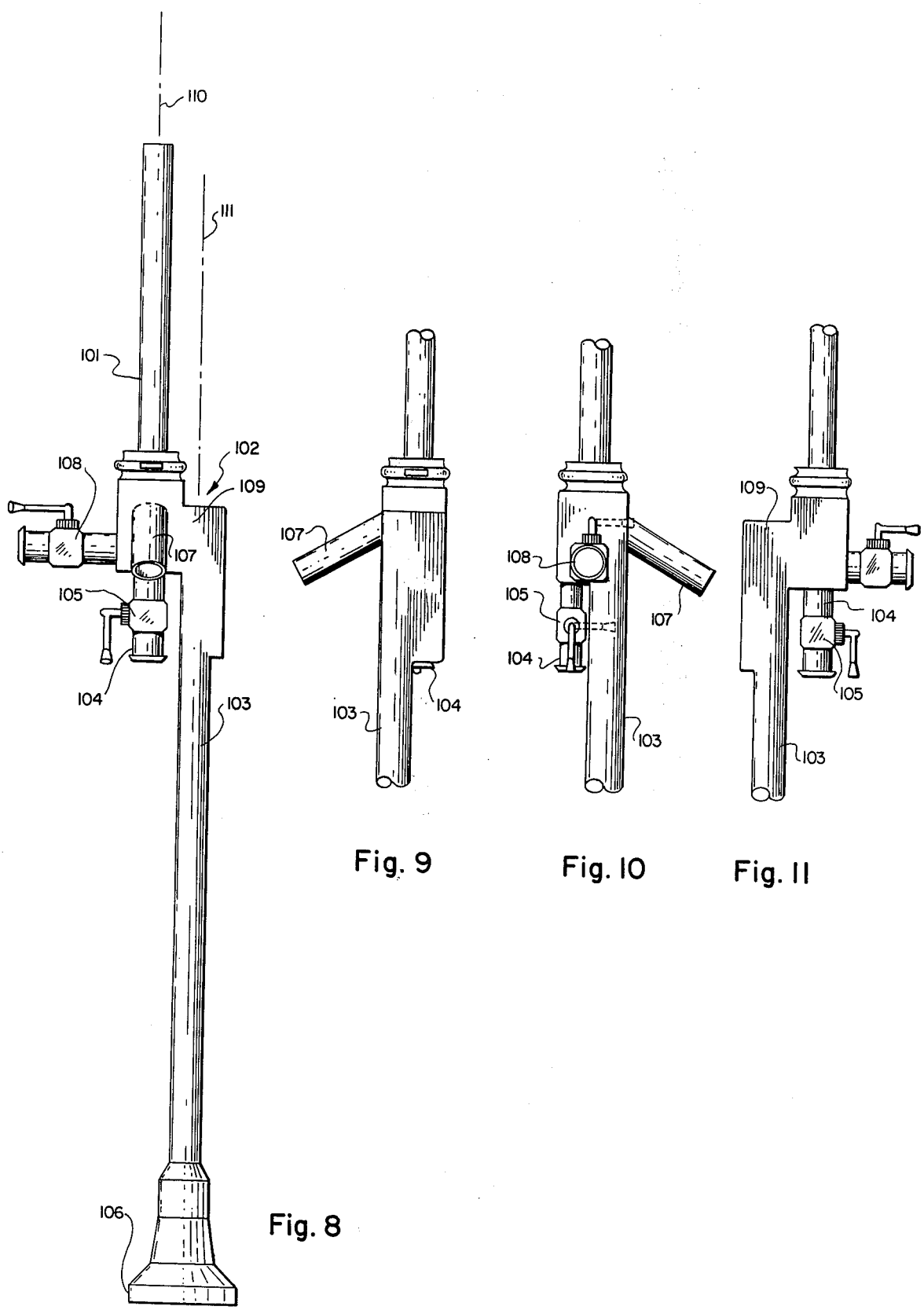
FIG. 8 is a view in elevation which illustrates an operating arthroscope of this invention viewed normal a vertical plane bisecting both the occular lens and the instrument channel.
FIG. 9 is a fragmentary view of the arthroscope of FIG. 8 rotated about its vertical axis 90° counterclockwise as viewed from its occular end.
FIG. 10 is a fragmentary view similar to FIG. 9 of the arthroscope of FIG. 8 rotated 90° clockwise.
FIG. 11 is a fragmentary view similar to FIGS. 9 and 10 of the arthroscope of FIG. 8 rotated 180°.

A portion 109 of the housing 102 is offset slightly, typically about 2 to about 4 centimeters along a reference plane intersecting the vertical axes 110, 111, respectively, of the bottom (terminal) segment 101 and the top (viewing) segment 103 of the sheath. This offset is best seen in FIGS. 8 and 11. The top segment 103 contains the occular portion of the lens system, and may be either monocular, as shown, or binocular.

Although the offset construction of this invention is useful for endoscopes generally, the flat rectilinear cross-section disclosed herein is highly preferred. A particular advantage of the rectilinear cross-section is that it permits the use of a much larger objective lens than is practical in a round barrel sheath intended for use within a knee joint. For example, a 2.95 mm optic system may be placed within a sheath constructed to accommodate a 3.5 mm instrument channel. Another important structural feature within contemplation is the use of a very short working length of sheath below the central housing. Operating arthroscopes with working lengths of less than 4 inches are entirely practical for knee surgery.

Although this disclosure has been directed specifically to arthroscopes and arthroscopy, with specific reference to certain illustrated embodiments, it is not intended thereby to limit the scope of the appended claims. It is within contemplation that the improvements disclosed and claimed herein may be adapted to endoscopes of various types. It is also contemplated that the teachings of this disclosure will lead directly to the development of practical instruments for the improved examination of smaller joints, such as those of hands or feet. In such instruments, certain design changes are to be expected.

I claim:

1. In an arthroscope with structural elements, including a lens system, an instrument channel and a fiber optic lighting system, fixed within a rigid sheath, the improvement which comprises:
   providing said sheath in association with a central housing, wherein the sheath includes
   a first, terminal, elongated sheath segment extending from said central housing said terminal segment having a longitudinal axis; and
   a second, viewing, elongated sheath segment carrying an eye piece at its distal end, extending in a direction opposite said terminal segment from said central housing at a location laterally offset from but approximately adjacent the longitudinal axis of said terminal segment, wherein
   said viewing segment is longer than said terminal segment, and
   said instrument channel is contained by said terminal sheath segment, and terminates with an entry, adapted to pass instruments from outside, at said central housing at a location offset from said viewing segment and spaced from said eye piece approximately the length of said viewing sheath segment;
   the relative length of said terminal and viewing sheath segments, and the spatial arrangement of said eye piece and said entry being selected so that blind manipulations of instruments through said instrument channel may be accomplished by an operator looking through the eye piece with said operator's hands in front of the operator's torso and below the shoulder level of said operator.

2. An improvement according to claim 1 wherein the cross-sectional perimeter configuration of the terminal segment of said sheath, as viewed from its distal end, is defined by a first pair of approximately parallel longer sides and a second pair of sides relatively shorter with respect to said longer sides.

3. An improvement according to claim 1 wherein the line of sight of said lens system is angled towards the longitudinal axis of the instrument channel.

4. An improvement according to claim 3 wherein the cross-sectional configuration of the terminal end of said sheath, as viewed from its distal end, has a major axis and a minor axis, and the instrument channel and the objective lens are spaced from each other to near the extreme ends of the major axis of said distal end of the sheath.

5. An improvement according to claim 1 wherein the longitudinal axis of said terminal segment is approximately parallel the longitudinal axis of said viewing segment and said axes are spaced from each other by a distance of between about 2 and about 5 centimeters.

6. An improvement according to claim 6 wherein the occular lens of the lens system is spaced longitudinally from the entry to the instrument channel by a distance no less than the distance from said entry to the distal end of said instrument channel.

7. An improvement according to claim 6 wherein the working length of the sheath below the central housing is less than about 4 inches.

8. An improvement according to claim 7 wherein the cross-sectional perimeter configuration of the terminal segment of said sheath, as viewed from its distal end, is defined by a first pair of approximately parallel longer sides and a second pair of sides relatively shorter with respect to said longer sides.

9. An improvement according to claim 8 wherein the cross-sectional configuration of the terminal end of said sheath, as viewed from its distal end, has a major axis and a minor axis, and the instrument channel and the objective lens are spaced from each other to near the extreme ends of the major axis of said distal end of the sheath.

10. An arthroscope according to claim 8 wherein the longitudinal axes are laterally spaced by a distance of between about 2 and about 4 centimeters.

11. An arthroscope according to claim 10 wherein the terminal sheath segment is less than about 4 inches long.

12. An arthroscope according to claim 10 wherein the occular lens is carried a distance longitudinally spaced from the entry to the instrument channel greater than the total length of the instrument channel.

13. An operating arthroscope, including:
a rigid elongated terminal sheath segment with a cross-sectional perimeter configuration as viewed from its distal end defined by a pair of approximately parallel longer sides and a pair of sides relatively shorter with respect to said longer sides;
a central housing connected to a proximal end of said terminal segment and adapted for connection to sources of light and irrigation fluid for delivery through components housed within said terminal sheath segment;
an instrument channel extending through said central housing and said terminal sheath segment; and
an elongated viewing sheath segment longer than said terminal sheath segment with a longitudinal central axis approximately parallel the corresponding axis of said terminal sheath segment and laterally spaced therefrom but approximately adjacent thereto connected at its proximal end to said central housing and carrying an occular lens at its distal end optically connected through said central housing to an objective lens carried by the distal end of said terminal sheath segment.

14. An arthroscope according to claim 13 wherein said longitudinal axes are laterally spaced by a distance of between about 2 and about 4 centimeters.

15. An arthroscope according to claim 14 wherein the terminal sheath segment is less than about 4 inches long.

16. An arthroscope according to claim 14 wherein the occular lens is carried a distance longitudinal spaced from the entry to the instrument channel greater than the total length of the instrument channel.

* * * * *